(12) United States Patent
Karpetsky

(10) Patent No.: US 7,429,731 B1
(45) Date of Patent: Sep. 30, 2008

(54) METHOD AND DEVICE FOR NON-CONTACT SAMPLING AND DETECTION

(75) Inventor: Timothy P. Karpetsky, Towson, MD (US)

(73) Assignee: Science Applications International Corporation, San Diego, CA (US)

( * ) Notice: Subject to any disclaimer, the term of this patent is extended or adjusted under 35 U.S.C. 154(b) by 0 days.

(21) Appl. No.: 11/580,876

(22) Filed: Oct. 16, 2006

Related U.S. Application Data

(63) Continuation of application No. 11/122,459, filed on May 5, 2005, now Pat. No. 7,138,626.

(51) Int. Cl.
*H01J 49/00* (2006.01)
*B01D 59/44* (2006.01)

(52) U.S. Cl. .................. 250/288; 250/281; 250/282; 250/286; 250/423 R; 250/424

(58) Field of Classification Search ........... 250/288, 250/281, 282, 286, 423 R, 424
See application file for complete search history.

(56) References Cited

U.S. PATENT DOCUMENTS

| | | | |
|---|---|---|---|
| 4,159,423 A | 6/1979 | Kambara | 250/423 R |
| 4,271,357 A | 6/1981 | Bradshaw et al. | 250/287 |
| 4,542,293 A | 9/1985 | Fenn et al. | 250/288 |
| 4,546,253 A | 10/1985 | Tsuchiya et al. | 250/288 |
| 4,789,783 A | 12/1988 | Cook | 250/379 |
| 4,855,595 A | 8/1989 | Blanchard | 250/287 |
| 4,948,962 A | 8/1990 | Mitsui et al. | 250/288 |
| 4,974,648 A | 12/1990 | Propst | 144/24.13 |
| 5,192,865 A | 3/1993 | Zhu | 250/288 |

(Continued)

FOREIGN PATENT DOCUMENTS

GB 2.127.212 4/1984

(Continued)

OTHER PUBLICATIONS

Chemi-Ionization—Mass Spectrometry Terms, "Chemi-Ionization" [online], Dec. 26, 2005 [retrieved on Apr. 28, 2006], 1 p., Retrieved from the Internet: http://www.msterms.com/wiki/index.php?title=Chemi-Ionization.

(Continued)

*Primary Examiner*—Nikita Wells
(74) *Attorney, Agent, or Firm*—King & Spalding LLP

(57) ABSTRACT

A system for the stand-off detection of trace amounts of analyte materials such as explosives, chemical warfare agents, toxic industrial chemicals, and the like includes an ion source that is operably connected to an ion collection means and to a sensor. The ion source employs a first gas that is passed through an electrical discharge to produce metastable gas molecules as well as charged particles of various kinds. Ions and other charged particles are removed from the first gas which is then reacted with a second gas having a lower ionization potential to obtain reactant ions of relatively uniform energy. The reactant ions are focused and accelerated into a beam that is directed upon a surface, such as luggage or clothing that is being interrogated, to produce analyte ions which are collected and passed into the sensor that is preferably a differential mobility spectrometer.

111 Claims, 7 Drawing Sheets

U.S. PATENT DOCUMENTS

| | | | | |
|---|---|---|---|---|
| 5,304,797 | A | 4/1994 | Irie et al. | 250/287 |
| 5,338,931 | A | 8/1994 | Spangler et al. | 250/287 |
| 5,485,016 | A | 1/1996 | Irie et al. | 250/288 |
| 5,541,519 | A | 7/1996 | Stearns et al. | 324/464 |
| 5,587,581 | A | 12/1996 | Stroosnyder | 250/287 |
| 5,684,300 | A | 11/1997 | Taylor et al. | 250/286 |
| 5,892,364 | A | 4/1999 | Monagle | 324/464 |
| 6,124,675 | A | 9/2000 | Bertrand et al. | 315/111.91 |
| 6,225,623 | B1 | 5/2001 | Turner et al. | 250/286 |
| 6,462,338 | B1 | 10/2002 | Inatsugu et al. | 250/292 |
| 6,495,823 | B1 | 12/2002 | Miller et al. | 250/286 |
| 6,512,224 | B1 | 1/2003 | Miller et al. | 250/286 |
| 6,649,907 | B2 * | 11/2003 | Ebeling et al. | 250/288 |
| 6,690,004 | B2 | 2/2004 | Miller et al. | 250/286 |
| 6,727,496 | B2 | 4/2004 | Miller et al. | 250/287 |
| 6,744,041 | B2 | 6/2004 | Sheehan et al. | 250/283 |
| 6,815,668 | B2 | 11/2004 | Miller et al. | 250/286 |
| 6,818,889 | B1 | 11/2004 | Sheehan et al. | 250/288 |
| 6,822,225 | B2 | 11/2004 | Xu et al. | 250/287 |
| 6,852,970 | B2 | 2/2005 | Yamada et al. | 250/288 |
| 6,867,415 | B2 | 3/2005 | Hughey et al. | 250/288 |
| 6,888,132 | B1 | 5/2005 | Sheehan et al. | 250/288 |
| 6,949,741 | B2 | 9/2005 | Cody et al. | 250/288 |
| 6,972,407 | B2 | 12/2005 | Miller et al. | 250/287 |
| 6,998,605 | B1 | 2/2006 | Frazer et al. | 250/281 |
| 7,005,634 | B2 | 2/2006 | Shiokawa et al. | 250/288 |
| 7,041,966 | B2 | 5/2006 | Frazer et al. | 250/281 |
| 7,053,367 | B2 | 5/2006 | Tobita et al. | 250/288 |
| 7,064,320 | B2 | 6/2006 | Yamada et al. | 250/288 |
| 7,078,068 | B2 | 7/2006 | Book | 426/140 |
| 7,091,493 | B2 | 8/2006 | Hiraoka | 250/425 |
| 7,095,019 | B1 | 8/2006 | Sheehan et al. | 250/288 |
| 7,112,785 | B2 | 9/2006 | Laramee et al. | 250/288 |
| 7,112,786 | B2 | 9/2006 | Russ, IV et al. | 250/288 |
| 7,138,626 | B1 * | 11/2006 | Karpetsky | 250/288 |
| 7,259,368 | B2 | 8/2007 | Frazer et al. | 250/281 |
| 7,274,015 | B2 | 9/2007 | Miller et al. | 356/508 |
| 2002/0185593 | A1 | 12/2002 | Doring | 250/287 |
| 2004/0245458 | A1 | 12/2004 | Sheehan et al. | 250/288 |
| 2005/0196871 | A1 | 9/2005 | Cody et al. | 436/173 |
| 2007/0084999 | A1 | 4/2007 | Miller et al. | 250/288 |

FOREIGN PATENT DOCUMENTS

| | | |
|---|---|---|
| GB | 2.288.061 | 10/1995 |
| JP | 05203637 | 8/1993 |
| WO | WO 93/14515 | 7/1993 |
| WO | WO 2004/098743 | 11/2004 |
| WO | WO 2006/011171 | 2/2006 |
| WO | WO 2006/122121 | 11/2006 |

OTHER PUBLICATIONS

Scott, R.P.W., "Gas Chromatography Detectors" [online], Part of the Chrom. Ed. Series, Subsection: Thermal Argon Detector, Copyright 2002-2005 [retrieved on Apr. 28, 2006], 7 pp., Retrieved from the Internet: http://www.chromatography-online.org/GC-Detectors/Ionization-Detectors/Thermal-Argon/rs61.html.

Scott, R.P.W., "Gas Chromatography Detectors" [online], Part of the Chrom. Ed. Series, Subsection: Macro Argon Detector, Copyright 2002-2005 [retrieved on Apr. 28, 2006], 10 pp., Retrieved from the Internet: http://www.chromatography-online.org/GC-Detectors/Ionization-Detectors/Macro-Argon/rs54.html.

Scott, R.P.W., "Gas Chromatography Detectors" [online], Part of the Chrom. Ed. Series, Subsection: Micro Argon Detector, Copyright 2002-2005 [retrieved on May 11, 2006], 6 pp., Retrieved from the Internet: http://www.chromatography-online.org/GC-Detectors/Ionization-Detectors/Micro-Argon/rs59.html.

Scott, R.P.W., "Gas Chromatography Detectors" [online], Part of the Chrom. Ed. Series, Subsection: The Helium Detector, Copyright 2002-2005 [retrieved on Apr. 28, 2006], 8 pp., Retrieved from the Internet: http://www.chromatography-online.org/GC-Detectors/Ionization-Detectors/Helium/rs64.html.

Akishev, Yu, et al., "Negative Corona, Glow and Spark Discharges in Ambient Air and Transitions Between Them," *Plasma Sources Sci. Technol.*, vol. 14, pp. S18-S25 (2005).

Willoughby, Ross C., et al., "Transmission of Ions Through Conductance Pathways from Atmospheric Pressure," *Proceedings of the 52nd ASMS Conference on Mass Spectrometry and Allied Topics*, Nashville, Tennessee, 2 pp., May 23-27, 2004.

Sheehan, Edward W., et al., "Atmospheric Pressure Focusing," *Proceedings of the 52nd ASMS Conference on Mass Spectrometry and Allied Topics*, Nashville, Tennessee, 2 pp., May 23-27, 2004.

Benocci, R., et al., "I-V Characteristics and Photocurrents of a He Corona Discharge Under Flow Conditions," *J. Phys. D: Appl. Phys.*, vol. 37, pp. 709-714 (2004).

Bokman, C. Fredrik, "Analytical Aspects of Atmospheric Pressure Ionization in Mass Spectrometry," Acta Universitatis Upsaliensis, *Comprehensive Summaries of Uppsala Dissertations from the Faculty of Science and Technology*, vol. 748, 46 pp., 2002.

Willoughby, R., Sheehan, E., Mitrovich, A., "A Global View of LC/MS," Global View Publishing, pp. 64-65, 470-471, Copyright 2002.

Hanley, Luke, et al., "Surface Mass Spectrometry of Molecular Species," *Journal of Mass Spectrometry*, vol. 34, pp. 705-723 (1999).

Niessen, W.M.A. and van der Greef, J., "Liquid Chromatography—Mass Spectrometry Principles and Applications," Marcel Dekker, Inc., New York, New York, pp. 339-341, Copyright 1992.

Bruins, A.P., "Mass Spectrometry With Ion Sources Operating at Atmospheric Pressure," *Mass Spectrometry Reviews*, vol. 10, pp. 53-77, 1991.

Beres, S.A., et al., "A New Type of Argon Ionisation Detector," *Analyst*, vol. 112, pp. 91-95, Jan. 1987.

Lovelock, J.E. and Lipsky, S.R., "Electron Affinity Spectroscopy—A New Method for the Identification of Functional Groups in Chemical Compounds Separated by Gas Chromatrography," *J. Amer. Chem. Soc.*, vol. 82, pp. 431-433, Jan. 20, 1960.

Lovelock, J.E., "A Sensitive Detector for Gas Chromatrography," *Journal of Chromatography*, vol. 1, pp. 35-46, 1958.

Lovelock, J.E., "Measurement of Low Vapour Concentrations by Collision with Excited Rare Gas Atoms," *Nature*, vol. 181, pp. 1460-1462, 1958.

"Principles of DC and RF Plasma Spraying" [online], 1 p., Retrieved from the Internet: http://wiv.vdi-bezirksverein.de/HenneVDI.pdf.

Leparoux, et al., "Investigation of Non-Oxide Nanoparticles by RF Induction Plasma Processing—Synthesis, Modelling, and In-Situ Monitoring," *EMPA-Thun, Materials Technology*, 1 p.

Guimbaud, C., et al., "An APCI Ion Source to Monitor $HNO_3$ Under Ambient Air Conditions" [online], 1 p., Retrieved from the Internet: http://lch.web.psi.ch/pdf/anrepo3/19.pdf.

Hart, K. J., et al., "Reaction of Analyte Ions With Neutral Chemical Ionization Gas," *Journal of the American Society for Mass Spectrometry*, vol. 3, No. 5, pp. 549-557, 1992 (ISSN 1044-0305).

Steinfeld, Jeffrey, I., et al., "Explosives Detection: A Challenge for Physical Chemistry," *Annual Review of Physical Chemistry*, vol. 49, pp. 203-232, Oct. 1998.

Stach, J., et al., "Ion Mobility Spectrometry—Basic Elements and Applications," *International Journal for Ion Mobility Spectrometry*, IJIMS 5(2002)1, pp. 1-21, 2002.

Duckworth, D. C., et al., "Radio Frequency Powered Glow Discharge Atomization/Ionization Source for Solids Mass Spectrometry," *Analytical Chemistry*, vol. 61, No. 17, pp. 1879-1886, Sep. 1, 1989.

* cited by examiner

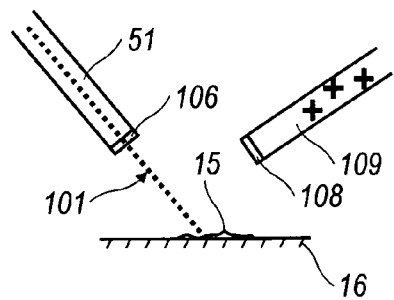
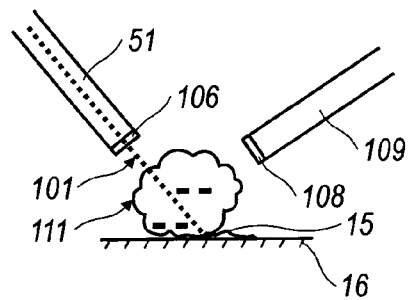
FIG. 9a  FIG. 9b
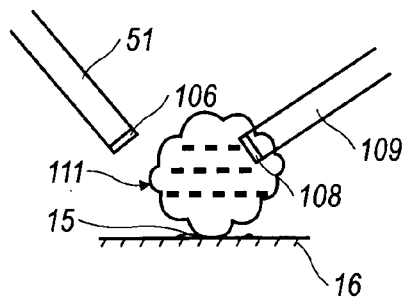
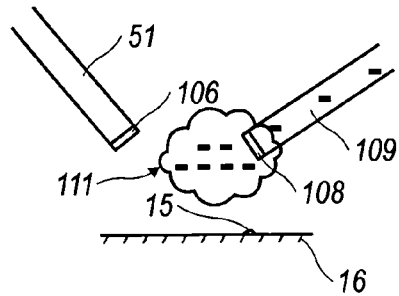
FIG. 9c  FIG. 9d

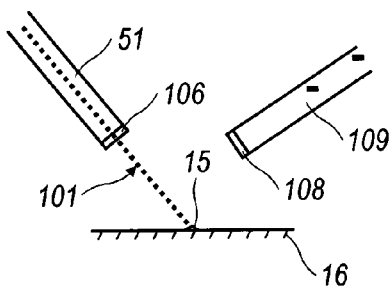
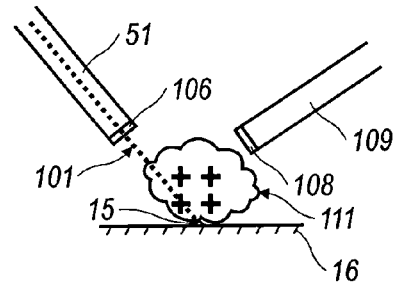
FIG. 10a        FIG. 10b
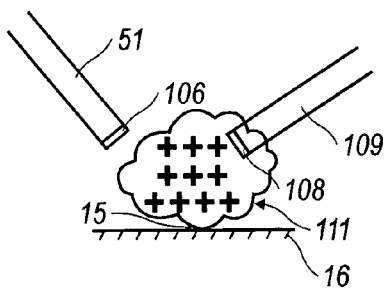
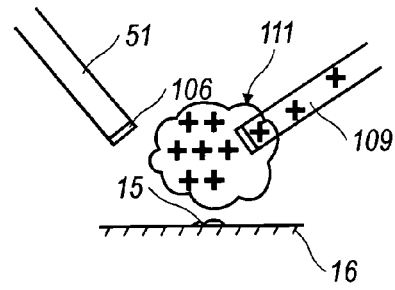
FIG. 10c        FIG. 10d

METHOD AND DEVICE FOR NON-CONTACT SAMPLING AND DETECTION

CROSS REFERENCE TO RELATED APPLICATIONS

This application is a continuation of U.S. Utility patent application Ser. No. 11/122,459 entitled "Method and Device for Non-Contact Sampling and Detection," filed May 5, 2005, now U.S. Pat. No. 7,138,626 the disclosure of which is hereby incorporated herein by reference in its entirety.

BACKGROUND OF THE INVENTION

1. Field of the Invention

This invention relates to a method and apparatus for the direct, non-contact, real-time sampling and detection of minute quantities of materials on surfaces.

More particularly, this invention relates to a method and apparatus for producing ions from targeted sample molecules on or above a surface that is spaced apart from the apparatus and for detecting and identifying those ions, all without contacting the surface.

2. Description of Related Art

Military and security needs, law enforcement concerns and environmental monitoring all require a capability to sample and detect minute quantities of explosives, drugs, chemical and biological agents, toxic industrial chemicals, and other targeted compounds of interest residing on or in a variety of materials and surfaces. Most users desire a fast, portable, simple, operator friendly detector that combines different detection capabilities in a single unit and that is capable of directly and automatically acquiring samples from surfaces, identifying targeted substances in those samples, and providing immediate operator notification that such substances are present or not.

Most explosives, chemical warfare agent, toxic industrial chemical and illicit substance detectors in use for security purposes depend upon the vapor pressure of the targeted material for detection. If vapor pressures of chemicals of interest are very low, they are undetectable by traditional screening methods or vapor must be produced from these materials. Consequently, using current technology, sample chemicals must be first collected from a surface by wiping or vacuuming. The wipes or vacuum filters must then be heated and the vapor introduced to a vapor detector for detection and identification of the chemicals present. These methods are time consuming, expensive and highly dependent upon trained operators capable of near perfect consistency in obtaining samples. These factors limit screening to only a small portion of the samples that should be examined.

The present invention provides a complete means to scan surfaces such as paper, plastics, skin, glass and textiles from variable distances and determine in seconds if targeted chemicals or materials are present, completely independent of the vapor pressures of such chemicals. Currently available detectors generally create ions of the vapors of targeted chemicals and other chemicals taken into the body of the detector, then separate the ions and detect, identify and provide notification of the presence of any targeted chemicals. The present invention overcomes this limitation by creating ions from sample chemicals exterior to the detector, on surfaces, and draws these ions into the detector for separation, detection, identification and notification.

In order to do this in an easy to use, yet economical configuration, reactant ions are created within the detector from a constant supply of conditioned air or other gas. These reactant ions are focused and accelerated as they leave the detector. The reactant ion stream impacts the chemicals on a surface exterior to the detector and creates surface sample chemical ions. These ions are drawn into another part of the detector, using electronic means to control ion movement and collection. Once within the detector, the surface sample chemical ions are separated from the ambient air in which they are collected, and simultaneously moved and concentrated in a stream of constant composition air. The ions are then detected and identified after movement into a micro differential mobility spectrometer having no moving parts and made much like an integrated circuit.

In seeking to develop a single device that would directly ionize samples on surfaces and subsequently detect and identify these sample ions, use was made of several precedents. For example, ion mobility spectrometers require an ion source, which may be a radioactive ionization source (β-emitter or electron producer) such as $^{63}$Ni. Because of the regulations associated with obtaining, transporting and maintaining equipment with radioactive sources, alternative ionization sources such as corona discharge ionization sources are preferred. Such a corona discharge is described in U.S. Pat. No. 6,225,623. Corona discharge units have been and are widely used with helium gas to produce long-lived metastable helium atoms. These excited state helium atoms are used to transfer energy to neutral molecules, thereby ionizing such neutral molecules. An exemplary detector that uses a corona discharge ionization source is described in the Cook patent, U.S. Pat. No. 4,789,783. Such corona discharge ionization detectors are commercially available from Finnegan, GOW-MAC, VICI and others.

A variation of the corona-type ionization source is described in International Application No. WO 2004/098743 A2. The source comprises a chamber having an inlet port and an outlet port for passage of a carrier gas, and a pair of electrodes arranged to create a corona discharge within the chamber. The carrier gas, helium or nitrogen, is passed through the corona discharge causing formation of, among other species, neutral, excited state, metastable species of the carrier gas. Those excited state carrier gas molecules upon leaving the device then contact the sample, or analyte, and by transfer of energy from the excited state carrier gas molecules to analyte molecules, produce analyte ions. The analyte ions in the carrier gas are then passed to a charged particle or ion sensor, which may be the sensing element of a mass spectrometer or an ion mobility spectrometer. In this teaching, the helium metastable atoms leave the confines of the device and subsequently react with surface materials to produce surface sample ions.

In the present invention, the neutral helium metastable and energetic atoms, freed of any ions produced in the corona discharge by ion filters, are then reacted with the chemical components of air or other gases such as dopants, introduced within the device, causing the formation of reactant ions, such as $O_2^-$ and $H_3O^+$, and electrons within the device. It should be noted that neutral metastable helium atoms can interact with other metastable atoms and with neutral ground state atoms to produce charged species. So, even if ion filters are used at this stage, ions can still be produced. The advantage of using filters is that they remove the ions produced during passage of the gas through the corona discharge. Subsequent charged species production results only from the interactions noted above. Alternatively, if ion filters are not used, ions produced in the corona discharge, along with energetic neutral species, are reacted with the chemical components of air or other gases, introduced within the device, causing the formation of reactant ions, such as $O_2^-$ and $H_3O^+$, and electrons within the device. This transfer and downhill flow of energy from (1) the corona to energetic atoms and ions, then (2) from energetic atoms and\or ions to ions of introduced gases, results in the production of reactant ions that can be controlled and used in "soft" ionization processes to produce significant populations of molecular ions and clusters from a very wide variety of chemicals.

Unlike helium metastable atoms, which carry no charge, these reactant ions are positively or negatively charged and can be focused and accelerated within the device, and after they leave the device, they can be moved towards or away from different parts of the device depending upon the potential applied to that part of the device. Furthermore, these reactant ions can react with most chemicals to produce ions from those chemicals. The electrons produced can also react with gases to produce reactant ions.

The capability to control the reactant ions through focusing and acceleration provides several useful practical advantages over other methods. First, automated distance information from a rangefinder can provide feedback control to the ion focusing and accelerating portions of the invention. For example, by using such feedback control to direct the electronic focusing to vary the width of the ion stream leaving the ion production device, the reactant ions created within the invention can be focused on a surface such that the same amount of ions per unit area hit the surface independent of the distance between the detector and the surface. This allows the operator freedom of movement of the detector away from and towards the surface with assurance that, regardless of position, the same amount of detector initiated reactant ions will generate the same amount of sample ions on the surface, and ultimately, the same sensor-driven signal within the detector. Second, the reactant ions created within the invention are those well known to react with a wide variety of chemicals of interest, to form predominantly molecular ions. Molecular fragmentation is kept to a minimum in this "soft" ionization process. This greatly simplifies the detection and identification process. Third, the reactant ions emitted from the detector can be confined within a sheath gas such that, in the transit between detector and surface, the integrity of the detector originated ion population is largely maintained and admixing with the ambient air between the detector and the surface sample is kept to a minimum.

Turning to the detection of the produced surface sample ions, a mass spectrometer would appear to be ideal because of its high sensitivity and resolution or selectivity. However, mass spectrometry requires large, heavy and expensive equipment making the technique impractical for applications that require portability. The most widely used analytical systems for detecting and monitoring explosives and chemical warfare agents, both by the military and for airport security, employ ion mobility spectrometry (IMS). Ion mobility spectrometers function by pulling a gas that contains molecules of the compounds of interest through an ionization source and then moving the ions produced through a sensor. Both the ionization source and the sensor are commonly incorporated within a cylindrical drift tube, which is divided into two parts. The first, or reaction, region contains the ionization source and is separated from the drift region by an electrical shutter or ion gate. In all cases, the sample molecules are directly subjected to the ionization source and, depending upon the sample and the intensity of the source, a wide variety of molecular fragments, as well as simple ions, are produced. Under the influence of an electric field, the mixture of reactant and product ions reaches an ion gate that separates the reaction region and the drift region. With a bias voltage applied, the ions are attracted to the ion gate and lose their charge. Then the bias is briefly turned off, and ions are transmitted into the drift region of the cell. The smaller, more compact ions have a higher mobility in the electrical field than the heavier ions, and therefore traverse the region and collide with the collector plate in a shorter time. The collector current is then amplified. Its magnitude, as a function of time, is proportional to the number of ions arriving at that moment. The time-of-flight or mobility enables the identification of different chemicals. There are several significant drawbacks to IMS including:

- Typical ion mobility spectrometer analysis cycles require 5-8 seconds from introduction of sample to alarm notification
- The percentage of ions produced that are actually detected is as low as 1% due to the ion gate, resulting in lower sensitivity
- Resolution among different ions is dependent upon the length of the drift region, making it difficult to miniaturize
- Reduction in the cross sectional area of the drift tube also decreases sensitivity, again making it difficult to miniaturize Despite those limitations, ion mobility spectrometers may be usefully employed with the ion source of this invention to produce portable, non-contact sampling systems.

Another charged particle or ion sensor that is coming into use employs differential mobility spectrometry (DMS). An example of a differential mass spectrometer is the MicroDMx manufactured by Sionex Corporation. This device has no moving parts and is microfabricated. Its small size allows for extremely fast clear down times and very rapid responses to the presence of ions. In differential mobility spectrometry, selectivity is significantly enhanced relative to other techniques of ion resolution and detection. DMS exploits the way in which the mobility of ions changes in response to changes in an applied variable high electric field, and this provides substantially more information relating to a molecule's identity than other methods, consequently leading to a significant reduction in false positives. Differential mobility spectrometry can detect positive and negative ions simultaneously and has superior sensitivity and selectivity capabilities relative to more commonly used sensors such as ion mobility spectrometers. DMS achieves superior selectivity relative to simple time-of-flight information employed in other detectors by using placement of ions within four-dimensional space constructed to examine changes in ion mobility as a function of changes in high electric field strength. Detection and identification are rapidly made and notification of presence or absence of targeted materials given in near-real time. Sensitivity is enhanced as well because as a range of compensation voltages in a DMS device are scanned the actual percentage of ions detected for any type of ion species is significantly higher (>10x) than in conventional IMS. The capability of DMS to continuously accept and analyze sample ions, without the need for the ion-gate used in IMS devices, also increases the percentage of ions detected and consequently increases its overall sensitivity. Therefore, the sensitivity of DMS is higher than that of conventional IMS, and DMS sensors have the capability to detect compounds in the parts per trillion ranges. Differential mobility spectrometry can be used to detect positive and negative ions simultaneously. This is important in cases where all surface sample ions created would be collected at the same time, or where positive and negative ions would be alternately collected for extremely short times. These attributes of DMS are very important for the detection of explosives or other dangerous or controlled materials on clothing, baggage, paper, etc. at security checkpoints. Detection of such materials must be rapid, but also must be done with virtually no false negatives such that-these materials go undetected when actually present, creating a potentially dangerous situation. There must also be virtually no false positives such that materials are detected when none are present, thereby closing down the checkpoint while the false positive is verified as erroneous. The selectivity of DMS for certain materials such as explosives can be enhanced by transferring ions from an incoming ambient air stream to an air stream of controlled composition, possibly containing a dopant chemical to further control the nature of the ion species in the stream.

Having considered the ion production and ion detection portions of the invention, it is then necessary to manage, in a complementary manner, the movement of the reactant ions from the detector to the surface and the subsequent collection and concentration of surface sample ions in another part of the detector in order to most efficiently use the ions produced within the invention and in order to maximize sensitivity of the invention. Issuing reactant ions of alternating charges as a function of time from the ion production device and biasing the ion outlet to the same charge of the reactant ions so the ions are "pushed" away from the ion outlet and towards the surface can accomplish this. In synchrony with the changing biasing of the ion production device, the ion collection device undergoes programmed biasing aimed at providing sufficient charge opposite to that of the produced surface sample ions, thereby "pulling" these ions toward the collection device and into the sensor for detection and identification. The maximum possible number of collected ions must reach the sensor to attain the highest sensitivity. In order not to lose ions through collisions with walls within the detector, the ions are focused such that they are transported without touching the walls. The possibility exists that reactant ions of one charge could form both positively and negatively charged surface sample ions. In this case, for each "burst" of reactant ions released on the surface sample, there would be two cycles of ion collection—one positive and one negative. This allows for the real-time collection of maximum information from the surface sample. The continuous detection of residual or unreacted reactant ions by the differential mobility spectrometer provides a means for feedback and other control of the detection system. For example, such feedback can be used, in conjunction with the distance from the detector reactant ion production device to the surface (provided by a rangefinder) to control the timing of changes of potential applied to the ion collection inlet, relative to those changes of potential controlling the production of reactant ions, as the distance between the detector and surface is changed. This has the practical effect of providing assurance that relatively the same number of ions is detected by the detector as it is moved toward or away from the surface. The operator, therefore, does not have to keep the detector at a fixed distance from the targeted surface and allows for freedom of movement of the detector toward or away from the surface with assurance that targeted surface materials will still be detected with relatively the same certainty. In the absence of a surface, i.e. if the targeted chemical is contained in the ambient air, feedback control without using the rangefinder but using the DMS signal, can be used to control the density of reactant ions projected from the ion production means, thereby controlling the overall sensitivity of the detector.

Using a means to generate ions of targeted chemicals on surfaces coupled with a small fast sensor with excellent sensitivity and selectivity, and the means to use distance and sensor information as feedback to control the entire process, provides the elements of a detector that can be used to close security loopholes. It will enable the rapid screening of the surfaces of people, baggage, cargo, parcels and vehicles at government and private facilities, transportation centers, checkpoints and borders, among others. It will also find use in substantiating illegal activities by facilitating the rapid and accurate detection of chemical warfare agents (CWAs), explosives and illicit substances and to verify decontamination efforts are successful by military personnel. Key features of the invention are means to control, focus and accelerate the detector originated reactant ions responsible for producing surface sample ions from chemicals on surfaces, and the coordination of these events with the rapid collection of the surface originated ions in high yields for detection and identification by the sensor. The capability to apply roughly the same amount of reactant ions to the same surface area regardless of the distance of the detector from the surface allows the operator to scan the surface from variable detector—surface distances and obtain the same result, rather than be constrained to holding the detector at a fixed, close distance from the surface.

Hence, it is an object of this invention to provide an ion production and sensor system that operates by impacting a reactant ion stream upon a surface to form ions of sample compounds carried on that surface, to collect at least some of the sample ions that are formed, and to pass those ions into, for example, a differential mobility spectrometer to identify and quantify the sample compounds.

Another object of this invention is to provide an extremely sensitive, fully portable, hand-held detector that can identify and quantify compounds such as drugs and chemical warfare agents in place on surfaces without physical contact of those surfaces.

Yet another object of this invention is to detect equally well the presence of sample compounds having extremely low or hugely different vapor pressures without physical contact of the surface that carries the sample compounds.

It is a further object of this invention to provide an improved reactant ion production means that can direct a beam of reactant ions upon a surface to produce sample ions from materials on the surface at atmospheric pressure and without physical contact.

Other objects and advantages of this invention will be evident from the following description of certain preferred embodiments.

SUMMARY OF THE INVENTION

The detector system of this invention includes two major parts. First is a reactant ion production device having the capability to produce reactant ions from introduced air or other gases, and to filter, focus and accelerate such reactant ions constrained within a sheath gas or not as appropriate, toward a surface, generating surface sample ions from the chemicals on that surface. Second is an ion collection device that collects surface sample ions produced by the interaction of reactant ions with sample chemicals on the surface. The ion collection device has the capability to transfer such sample ions from the ambient air in which they are collected to a controlled air stream, to introduce reactant gases or dopants that can modify the structure, charge and/or adduct formation or dissociation of the sample ions, and to introduce the ions into a differential mobility spectrometer. Events in the ion production and ion collection devices are fully coordinated to maximize sample ion production and collection. Feedback controls, using information from a rangefinder and the spectrometer or sensor, enable similar ion detection results to be obtained regardless of the distance between the detector and the surface.

BRIEF DESCRIPTION OF THE DRAWING

FIGS. 9a through 9d depict the first half of a cycle of the production of ions, showing the production of negatively charged reactant ions, creation of negatively charged surface sample ions and collection of such surface sample ions using the reactant ion production means of FIGS. 2, 3 and 4, and the surface sample collection, detection and identification means of FIGS. 7 and 8 when operated in a pulsed mode;

FIGS. 10a through 10d depict the second half of a cycle of the production of ions, showing the production of positively charged reactant ions, creation of positively charged surface sample ions and collection of such surface sample ions using the reactant ion production means of FIGS. 2 3 and 4, and the surface sample collection, detection and identification means of FIGS. 7 and 8 when operated in a pulsed mode.

DESCRIPTION OF PREFERRED EMBODIMENTS OF THE INVENTION

Figure 1:
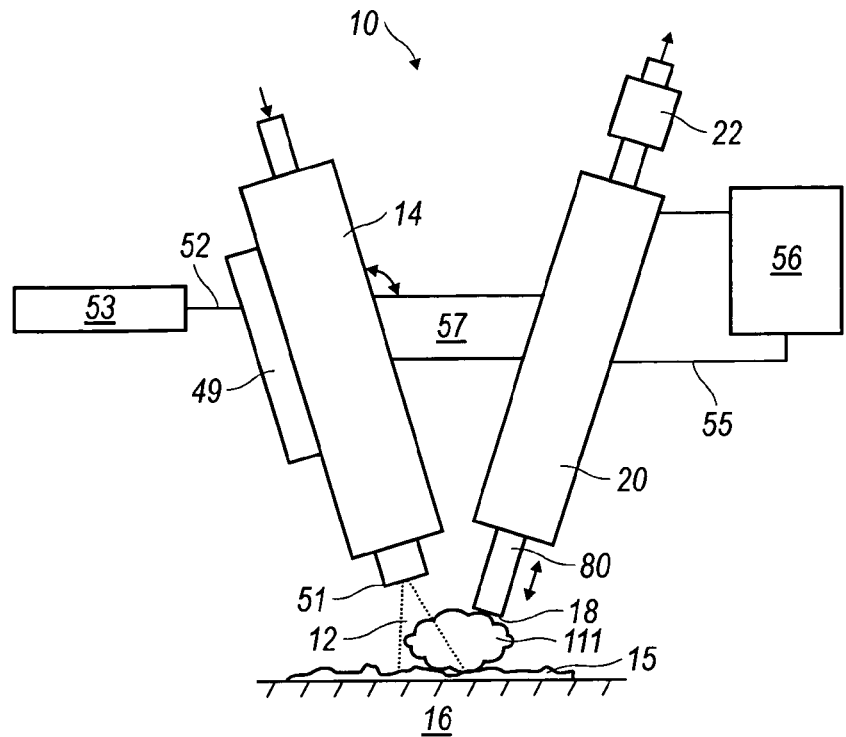
FIG. 1 is a schematic representation showing the arrangement of the reactant ion production and surface sample ion collection, detection and identification means according to this invention.

In a broad sense, this invention can be viewed as a method and means for conducting a three-step energy transfer process that may then be followed by an analytical procedure. Energy is applied to a first gas by means of a corona discharge, forming ions and other energetic species of that gas. The energetic species of the first gas then transfer energy to a second gas, which must have at least one component with an ionization potential, or ionization energy, less than that of the energetic species of the first gas so as to produce reactant ions of the second gas. Those reactant ions are caused to impact upon a surface, reacting with chemicals or other materials on the surface to produce analyte ions that are collected, detected and identified.

A significant advantage of this downhill energy flow is that it utilizes energy from an inexpensive, relatively uncontrolled high energy source (corona discharge) and converts it into energetic species that provide a "soft" ionization of analytes. That is, the reaction of Gas 2 reactant ions with analytes produces mainly molecular ions rather than ionized structural fragments. This simplifies the detection and identification process in a wide variety of situations.

Another advantage to using intermediate gases to ionize surface analytes is that the use of different gases can affect the population of surface analytes that is ionized, as well as the nature of the surface analyte ion ultimately detected. For example, the corona discharge can be used to produce energetic helium metastable atoms (ionization potential=20.6 e.V.). Then, these energetic atoms can transfer energy to the components of air having lesser ionization potentials (nitrogen, 15.6 e.V.; oxygen, 12.1 e.V.; water, 12.6 e.V.), producing reactant ions. These reactant ions can ionize a wide variety of organic chemicals. Selectivity can be achieved by changing the gas from air to other gases having different ionization potentials, such as ammonia, 10.2 e.V.; acetone, 9.7 e.V.; or di n-propylamine, 7.8 e.V. Reactant ions from each of these gases would ionize organic chemicals having ionization potentials less than that of the respective gas. This provides for selectivity based on ionization potential. Furthermore, the gas ions or neutral species can combine with the surface analyte ions to produce ion/molecular clusters that can aid in analyte ion identification and separation.

Electronic potentials at different places are used to manipulate the types and populations of reactant ions formed and issued from the reactant ion production device and of the types and populations of surface sample ions collected by the surface sample ion collection device. Also, real-time distance of detector to surface information, and detector sensor information provide automatic feedback control of these potentials. This feedback control manages and maximizes the instantaneous active interplay between the detector and the surface sample under investigation. On one hand, the reactant ion density put on the surface sample is maintained relatively constant and independent of working distance between the detector and the surface sample. On the other, the collection efficiency of the surface sample ion collector is optimized and collected ion loss prior to entry into the sensor is minimized. These events are automatically managed and coordinated such that operator input to the process is not necessary.

Turning now to specific embodiments of the invention, the detector system 10 of FIG. 1 operates at ambient pressure, without sample contact, by producing a stream 12 of either ions or a mixture of ions and metastable excited state molecules, in ion production means 14. Stream 12 is then directed toward a sample material 15, in place on surface 16, to produce ions of the sample material, some of which are detached from the surface and admixed with the gas adjacent the surface. A stream of gas is then pulled into a port means 18 of ion collection means 80 leading to ion detection and identification means 20 by action of pump 22.

Figure 2:
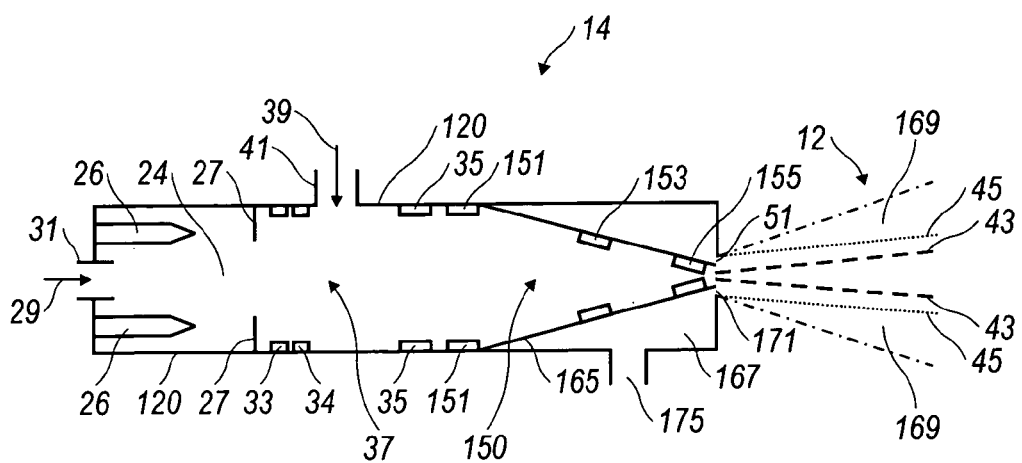
FIG. 2 is a schematic representation of a first reactant ion production means of the FIG. 1 system.
Figure 3:
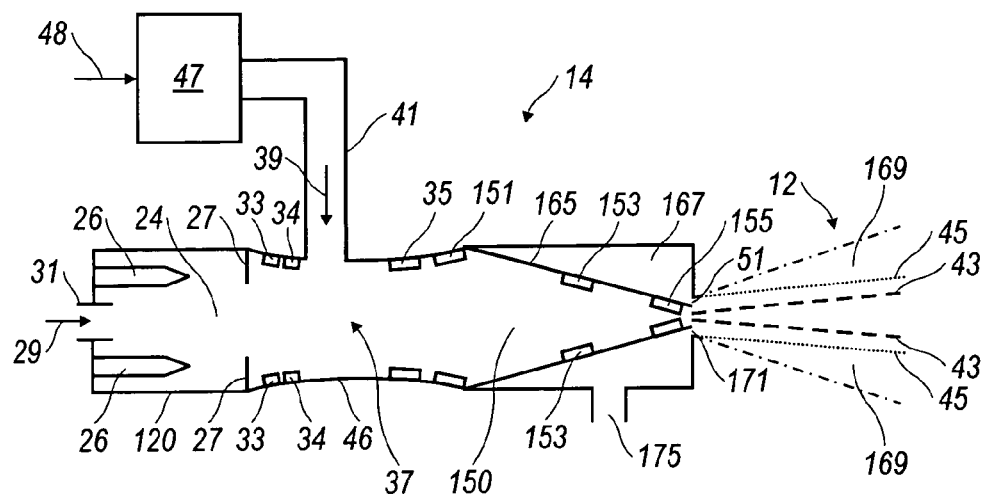
FIG. 3 is a schematic representation of another embodiment of the reactant ion production means of FIG. 2.
Figure 4:
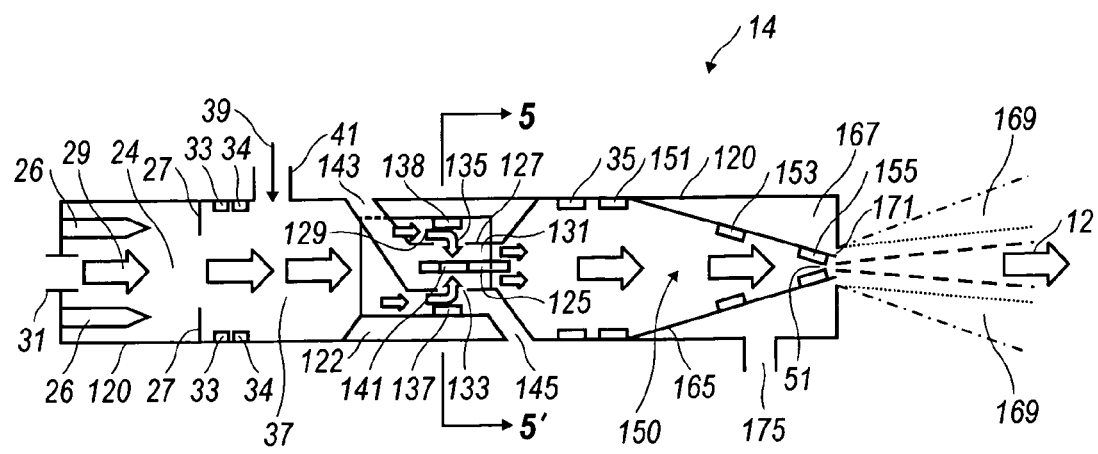
FIG. 4 is another embodiment of the reactant ion production means of FIGS. 2 and 3, including a means for concentrating ions and changing the ion carrier gas as is illustrated in FIG. 8.

Referring now to FIGS. 2, 3 and 4 as well as to FIG. 1, there is shown various embodiments of ion production means 14 which suitably may be constructed as a cylinder having a wall member 120 and arranged for generally axial flow of gases therethrough. A corona discharge is produced at the upstream end by ion production means 14 in space 24 located between corona discharge needles 26 and corona disk electrode 27. A first stream of gas 29, suitably either helium or argon among others, and possibly containing dopant chemicals, is introduced into ion production means 14 by way of first port 31 and is passed through the corona discharge in space 24 to thereby generate relatively long-lived, metastable helium or metastable argon atoms. A pair of filtering electrodes, 33 and 34, is placed just downstream from the corona discharge. One of those electrodes is positively charged and the other negatively charged and the two serve to remove ions that were created in the corona discharge area but do not interact with the metastable atoms as those carry no charge.

A reaction space 37 is provided just downstream from filtering electrodes 33 and 34 wherein gas stream 29, carrying excited metastable atoms, mixes with a second gas stream 39 entering into space 37 by way of port 41. Second gas stream 39 is preferably air, including clean dry air from a filtering device containing dessicant, but may comprise other gases or mixtures of gases depending upon the application. Metastable atoms of first gas 29 react with the second gas 39 to produce an array of positive and negative ions. The ions that are produced in space 37 are then accelerated in a downstream direction and focused into a coherent stream by action of electrodes 35, 151, 153 and 155. Ions exit ion production means 14 in a conical stream 12 that can be focused to form a cone 43 with a small apex angle, or to form a cone 45 with a larger apex angle.

A space 150 is provided adjacent the terminal end of the ion production means. Space 150 contains a plurality of accelerating and focusing electrodes 35, 151, 153, and 155 (FIG. 4), that cause the ion stream to exit the ion production means 14 at port 51 as a tight, coherent conical beam 12. The terminal portion of space 150 is advantageously formed with a conical tapered wall 165 that regularly decreases in diameter from the inner side of wall member 120 to the exit port 51. That structure forms a manifold 167 around the outside of wall 165 which functions to provide a flow of gas 169 from inlet 175 through a ring orifice 171 that encircles the exit port 51, producing a generally conical gas sheath that surrounds the ion stream. Gas flow 169 provides a protective sheath that helps to prevent reaction of the ion beam 12 with contaminant compounds.

FIG. 3 depicts an embodiment of the ion production means 14 in which the central portion 46 is formed as a venturi so that an air stream is drawn through port 41 into the body of means 14 by the reduced pressure created by flow of first gas stream 29 through venturi area 46. This arrangement avoids the need for a pump or other means to provide air to the device. A filter means 47, having an entry 48 and preferably containing a desiccant, is located upstream from port 41 so as to provide a dean air stream of uniform humidity to the ion production means. Water vapor is ionized by the excited species produced in the corona discharge so variations in humidity in the air entering means 14 can introduce undesirable variations in the ion population discharged from the unit.

Figure 5:
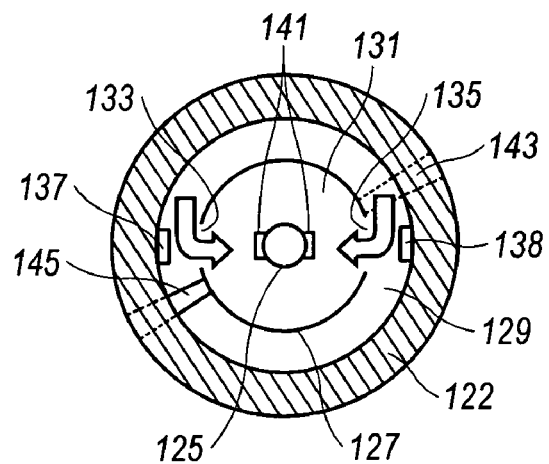
FIG. 5 is a cross sectional view of the ion production means of FIG. 4 taken along line 5-5'.

Yet another embodiment of the ion production means 14 is illustrated in FIGS. 4 and 5. FIG. 5 is a cross-section taken along line 5-5' of FIG. 4. Means 14, in this embodiment, includes ion concentration and gas exchange means, located centrally between reaction space 37 and terminal end space 150, that serve to strip ions from the helium stream and transfer those ions to a different gas, which suitably is purified air which may contain a dopant chemical to influence the nature of the ions. The ion concentration and gas exchange means is provided with a cylindrical outer wall 122, a central, axially aligned electrode carrier 125, and a cylindrical partition member 127 that serves to form a first annular space 129 that is open at its upstream end to accept the mixed and reacted gas from space 37. A second annular space 131 is formed between partition member 127 and axial electrode carrier 125. Partition member 127 is provided with two ports 133 and 135 that conveniently may be placed opposite one another to allow ion and gas flow between the first and second annular space.

A pair of electrodes 137 and 138, having the same polarity as the incoming ions contained in the gas issuing from space 37, is located on the inner side of wall 122 within annular space 129 just opposite ports 133 and 135. An electrode 141, of opposite charge to electrodes 137 and 138, is located on electrode carrier 125 in alignment with ports 133 and 135. As the ions in the gas stream within annular space 129 approach electrodes 137 and 138, they are directed toward and through ports 133 and 135. At the same time, the ions are attracted toward electrode 141 which tends to pull ions from the gas in space 129, through the ports, and into annular space 131. Meantime a flow of gas, suitably cleaned and dried air, is continuously introduced into annular space 131 by way of entry 143 that is located upstream of ports 133 and 135. After transfer of ions from the gas stream in space 129 to the gas flowing in annular space 131, the ion-depleted gas stream is exhausted to the atmosphere by way of exhaust port 145 that is located downstream of ports 133 and 135 while the ion-enriched gas stream exits annular space 131 into the ion accelerating and focusing space 150. The relative cross sectional areas of annular spaces 129 and 131 and the flow rates of the gas streams in those annular spaces can be adjusted such that the ion concentration in the gas within annulus 131 is substantially greater than that of the gas in annulus 129. Furthermore, by maintaining the pressures of the two gas streams such that there is a small but constant bleed of gas from space 131 into space 129, essentially all of the helium entering the system is rejected and exhausts through port 145. The ion stream produced may be either positive or negative depending upon the polarity applied to the various electrodes.

Returning to FIG. 1, a preferred embodiment of this invention employs a laser, or other type of, range finder 49 that is mounted in fixed association with ion production means 14. This embodiment is especially desirable in those instances wherein the device of this invention is configured as a compact, light, hand-held detector system for use in screening individuals, luggage, clothing and similar items without physical contact of any sort. Range finder 49 continuously determines the distance between the exit port 51 of the ion production means and the surface sample 15. Information stream 52 from the range finder is transmitted to processing unit 53 which may then use that information to adjust the focusing and acceleration functions of electrodes 35, 151, 153, and 155, so as to maintain the area of surface 16 impacted by the conical ion beam relatively constant as the distance between exit port 51 and surface sample 15 is changed. That result is accomplished by increasing the apex angle of the ion beam at short distances, on the order of an inch or so, between port 51 and surface sample 15, and decreasing the apex angle at greater distances, up to five to six inches between the port and surface sample. Also, feedback 55 from spectrometer 20 may be processed in a second controller means 56 to maximize ion content of sample gas entering the spectrometer by changing the attitude and location of ion collection/spectrometer entry port 18 relative to the exit port 51 of ion production means 14 through action of servo means 57.

Figure 6:
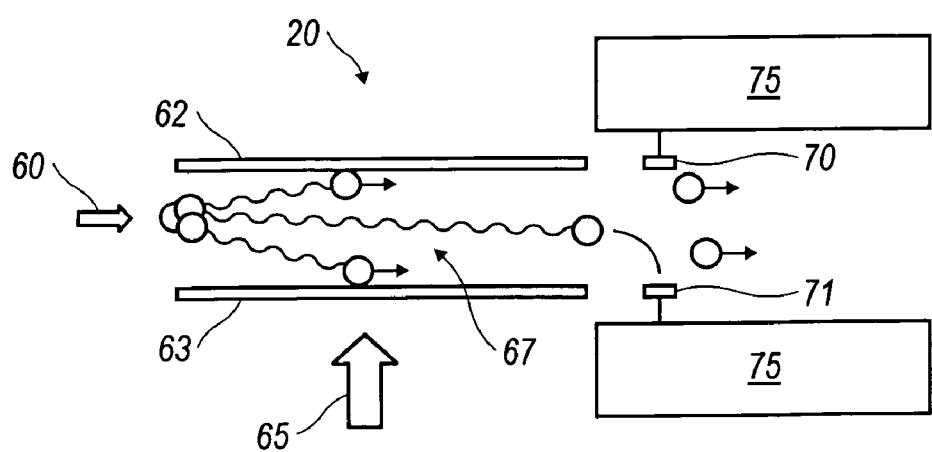
FIG. 6 is a diagrammatic representation of a surface sample ion detection and identification means according to the present invention.
Figure 7:
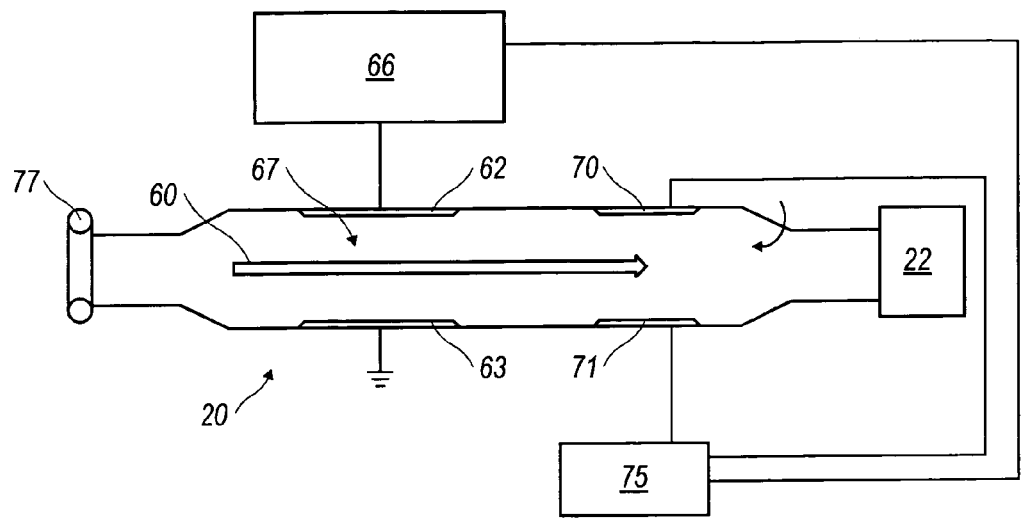
FIG. 7 is a partial, cross sectional representation of the surface sample ion detection and identification means of FIG. 6.

Ion detection and identification means 20 is preferably a miniaturized differential mobility spectrometer that is schematically illustrated in FIGS. 6 and 7 of this application and that is described in U.S. Pat. No. 6,512,224 to Miller et al, the entire disclosure of which is incorporated herein by reference. The differential mobility spectrometer that is described in the Miller et al patent is commercially available from Sionex Corporation. It is microfabricated in a manner analogous to the manufacture of a printed circuit and is in the form of a planar array having an overall size on the order of 36×72 mm, with a plate spacing of about half a millimeter.

Detector 20 is shown in schematic cross-section in FIGS. 6 and 7 and comprises a microfabricated planar array that forms an ion filter having no moving parts. A stream of ions 60, carried in a gas, is flowed between filter plates 62 and 63 of sensor 20. An asymmetric oscillating RF field 65 is applied perpendicular to the ion flow path 67 between filter plates 62 and 63 to impart a zigzag motion (FIG. 6) to the ions. At the same time, a DC compensation voltage is applied between plates 62 and 63 to control the motion of the ions such that some travel all the way through the plate array and are detected by electrodes 70 and 71, while others are directed to one or the other of plates 62 and 63 and are neutralized.

Two or more detector electrodes are located downstream from the filter plates. One of the electrodes, 70, is maintained at a predetermined voltage while the other of the electrodes 71 is typically at ground. Electrode 70 deflects ions downward to electrode 71 where they are detected. Depending upon the ion and upon the voltage applied to the electrodes, either electrode 70 or electrode 71 may be used to detect ions or multiple ions may be detected by using electrode 70 as one detector and electrode 71 as a second detector. In this way, both positively and negatively charged ions can be detected simultaneously. The output of the detector electrodes is transmitted to an electronic controller 75 where the signal is amplified and analyzed according to algorithms that serve to identify the ion species. Also, there may be provided an entry port electrode 77 to which either a positive or negative charge may be applied so as to attract oppositely charged ions toward and into the ion detection means 20.

Figure 8:
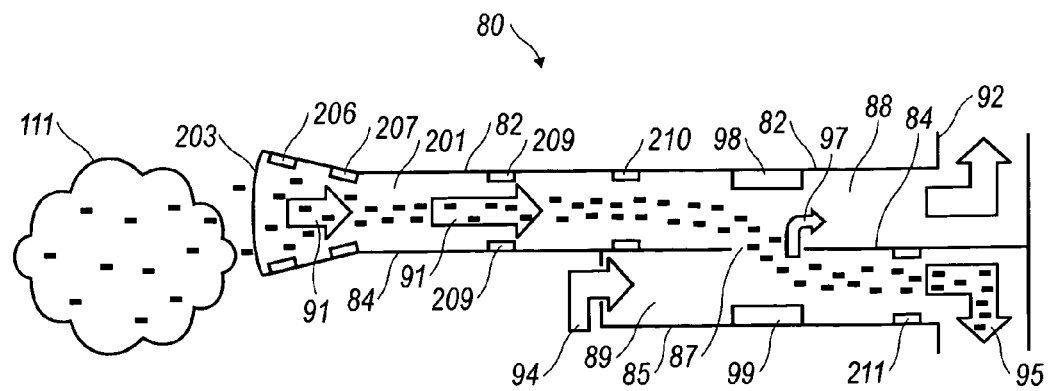
FIG. 8 is a cross-sectional representation of an ion inlet arranged with a surface sample ion concentration and change of ion carrier gas means for use with the detection and identification means of FIGS. 6 and 7.

Ion detection sensitivities may be increased as much as 10-fold or more through use of an ion inlet and concentration means 80 shown in diagrammatic cross section in FIG. 8. This device may comprise port means 18 of FIG. 1, and includes the functional equivalent of the ion concentration and gas exchange means employed in the ion production device that was illustrated in FIGS. 4 and 5. It serves to draw sample ions into the inlet and to change the gas containing the ions from ambient air collected at and near the sample and of uncontrolled composition, to air or other gas of defined composition, alone or in combination with other gases, including dopants such as methylene chloride and the like, which can be ionized using a very small UV lamp elsewhere in the detector.

Means 80 includes an inlet portion 201 that comprises a conduit having an upper wall 82 and a lower wall 84. A conductive, apertured entry 203 is provided at one end of the conduit to which a polarity and potential sufficient to attract the incoming ions contained in adjacent reaction cloud 111 is applied. Electrodes 206 and 207 are disposed around the inner periphery of conduit 201 just downstream of entry 203 and are of polarity and potential sufficient to attract and focus incoming surface analyte ions. Preferably the potential applied to entry 203 and to electrode 206 are similar and that of 207 is higher. Additional electrodes 209 and 210 are disposed around the inner periphery of conduit 201 further downstream from the entry. These last electrodes carry a controllable potential that is of the same polarity as is the incoming ion stream and serve to focus the ions into the central area of the conduit.

Reaction cloud 111 comprises a mixture of the gas issuing from the ion production means 14 and the ambient atmosphere, and contains sample ions formed by interaction of energetic ions from means 14 with sample materials 15 in place on surface 16. A stream of gas 91, comprising reaction cloud 111, is drawn through conduit 201 by action of pump 22 (FIG. 1), and the ion concentration in that gas stream is increased due to the attractive influence of the potential field created by the charge applied to inlet 203.

The gas exchange portion of means 80 comprises a two-chamber conduit formed by a partition wall portion 85 that is disposed exterior to and generally parallel with conduit walls 82 and 84. An orifice 87 located between the chamber ends is arranged to allow gas flow between upper chamber 88 and lower chamber 89. A flow of ions in the ambient sample atmosphere 91 is directed into the entry of the upper chamber 88. The ambient sample atmosphere with ions removed exhausts from the chamber 88 end at 92. Meanwhile, a second gas stream 94, for example, suitably preconditioned dry air, is directed into the entry of the lower chamber 89. Gas stream 94 passes through chamber 89 and the exiting flow 95 is then directed into the entry of ion detection means 20. The cross sectional area of chamber 88 relative to chamber 89 and the flow rate of sample atmosphere 91 relative to the flow rate of the second gas stream 94 are adjusted such that there is a small and constant bleed 97 of gas from the lower chamber 89 into the upper chamber 88 through the orifice 87.

A first electrode 98 having the same polarity as the incoming ions in sample stream 91 is located within chamber 88 above the orifice 87, while a second similar electrode 99, having a polarity opposite to the incoming ions, is located within chamber 89 below the orifice. As the ions in sample stream 91 approach electrode 98, they are repelled and are directed toward and through orifice 87. At the same time, the ions are attracted toward electrode 99, which tends to pull ions from sample stream 91 through the orifice and into gas stream 94. There may also be provided one or more guiding or focusing electrodes 211 located in chamber 89 downstream from orifice 87 to shape or accelerate the ion stream. By adjusting the flow of gas stream 94 to a level substantially less than the flow of gas stream 91, a concomitant concentration of ions in stream 94, to a level as high as ten fold of that of sample stream 91, is achieved. In addition to ion concentration, there is achieved a fairly complete elimination of helium or argon from the gas stream that enters sensor 20 in those situations where either helium or argon is present in the reaction cloud 111.

As was set out previously, a preferred ion detector 20 is a microfabricated differential mobility spectrometer that typically has a plate spacing on the order of half a millimeter. That small plate spacing allows use of much higher electric fields than are usual in other detector systems such as those employing ion mobility spectrometers; e.g. as high as about 35,000 V/cm compared to about 600 V/cm. Higher variable electric fields allow the changes in the mobility of ions as a function of field strength to be exploited to enhance selectivity and resolution. However, the maximum electric field is limited by the voltage at which arcing between the plates occurs with resultant destruction of the detector. Arc over occurs at a much lower voltage with helium or argon than with air. Consequently, removal of helium and argon from the sample gas stream that is analyzed allows for operation of the detector at higher field voltages thus further increasing the selectivity of the system.

A number of other synergistic advantages are obtained through the combination of the described ion production and concentration means with this particular detector. First of all, the ion production means of this invention does not use radioactive elements for ion creation and is therefore free of the regulatory burden imposed on devices employing radioactive sources. The corona discharge production of metastable helium atoms followed by the reaction of those metastable atoms with air to produce ions which in turn are used to ionize molecules of the sample is on the order of 1000 times more efficient than are those approaches that use the standard radioactive nickel or americium sources. Because the system of this invention creates far more ions of the sampled material than do conventional ion sources and because the preferred detector examines far more of the ions that are produced, fewer false positives or negatives result and superior resolution of targeted chemical ions from interferents is obtained.

In another embodiment of this invention, both the ion source and the ion collection means and detector are operated in a pulsed cyclic mode. In this mode, ion production and collection can be seen as two half cycles, the first half cycle being diagrammed in FIG. 9 and the second half cycle being diagrammed in FIG. 10. Referring now to FIG. 9a, a gas stream 101 carrying negatively charged reactant ions issues from the outlet 51 of the ion production device 14 and is directed toward surface 16 having a sample material 15 deposited thereon. Stand off distance between outlet 51 and surface 16 may conveniently range from less than one inch to six inches or more, thus allowing a non-contact and non-destructive inspection of the surface for the presence of the sample material.

Ion production device 14 is configured to produce reactant ions of predominately one charge; in this case it is producing negative ions. A negative potential is applied to an electrode 106 that is located at the tip of outlet 51. That negative charge acts to accelerate the negative ions contained in the gas stream issuing from outlet 51 toward surface 16. A similar electrode 108 is located at the tip of ion collection means and/or detector inlet 109. Inlet 109 may comprise either the inlet to ion detection means 20, in which case electrode 77 of FIG. 7 and electrode 108 are the same, or it may comprise an inlet means 203 to ion concentrator 80 of FIG. 8. The potential on electrode 108 at this stage of the cycle is zero or ground potential. Also, the negative pressure at the detector inlet 109 may be decreased during this time so as not to pull gas and ions from stream 101 toward the detector inlet.

The next stage of the cycle is depicted in FIG. 9b. Electrode 106 remains at a negative potential and electrode 108 remains at zero potential. A reaction cloud 111, typically comprising a mixture of air and helium and containing negatively charged surface sample ions, among other species has formed above the surface that is being examined. Thereafter, as is diagrammed in FIG. 9c, the reactant ion production pulse has ended. A negative potential is maintained on electrode 106 while the potential on electrode 108 is changed from zero to positive and the negative pressure at the detector inlet is increased. Electrode 108 is shaped and charged to produce an electric field that has the effect of drawing the ions in reaction cloud 111 toward the detector inlet. As shown in FIG. 9d, before the ion loud reaches electrode 108, its potential can be switched from positive to neutral so as to not destroy the oncoming negative ions by collision. Alternatively, the potential on electrode 108 can be left on and the collisions of ions with walls avoided by focusing the ions within the ion collection means as shown in FIG. 8. At the same time, the negative pressure at the ion inlet is increased to thereby capture much of the ion cloud and deliver it as a pulse to the ion detector. Optionally but preferably, the ion cloud pulse is delivered first to ion concentrator 80 and then to the differential mobility spectrometer.

The second half cycle is the obverse of the first half cycle, and is diagrammed in the steps shown in FIGS. 10a through 10d. Ion production device 14 is now configured to produce positive reactant ions, which are carried in the helium stream 101 issuing from outlet 51. The potential applied to electrode 106 remains positive throughout the entire half cycle, first accelerating positive ions toward the surface 16 and thereafter repelling the reaction cloud 111. Flow of the reactant ion stream 101 is ended after formation of the reaction cloud. The potential applied to electrode 108 is briefly switched to negative (FIG. 10c). The shape and charging of electrode 108 is sufficient to attract positive ions, including those formed from the sample material 15, toward inlet 109. At the same time, a negative pressure is applied to inlet 109, drawing the reaction cloud toward and into the inlet. The potential of electrode 108 can be then switched from negative to neutral (FIG. 10d) before the ion cloud reaches the electrode so as to minimize destruction of the positive ions. Alternatively, the potential on electrode 108 can be left on and the collisions of ions with walls avoided by focusing the ions within the ion collection means as shown in FIG. 8. Thereafter, the reaction cloud is delivered as a pulse to the ion concentrator or detector.

Cycle length can be varied over a fairly large range as the time for completing a cycle depends upon a number of controllable factors. Those factors include standoff distance between the ion outlet and the sample surface, gas flow rate delivered by the ion production means, and the configuration of the gas exit orifice. Generally speaking, a cycle can be completed in as little as 0.5 seconds or extended to several seconds in length. It is usually advantageous to maintain cycle times as short as possible. Cycle time can be controlled by feedback from the differential mobility spectrometer. The timing of detection of certain reactant ions indicates the place in the cycle, allowing for automatic adjustment of the controls determining cycle time.

Furthermore, it may be advantageous in certain situations to have a positive ion and a negative ion collection cycle for either or each of the positive or negative reactant ion production cycles. In this manner, information concerning both positive and negative surface sample ions produced in response to either positive or negative reactant ions can be obtained and used for identification purposes.

Figure 11:
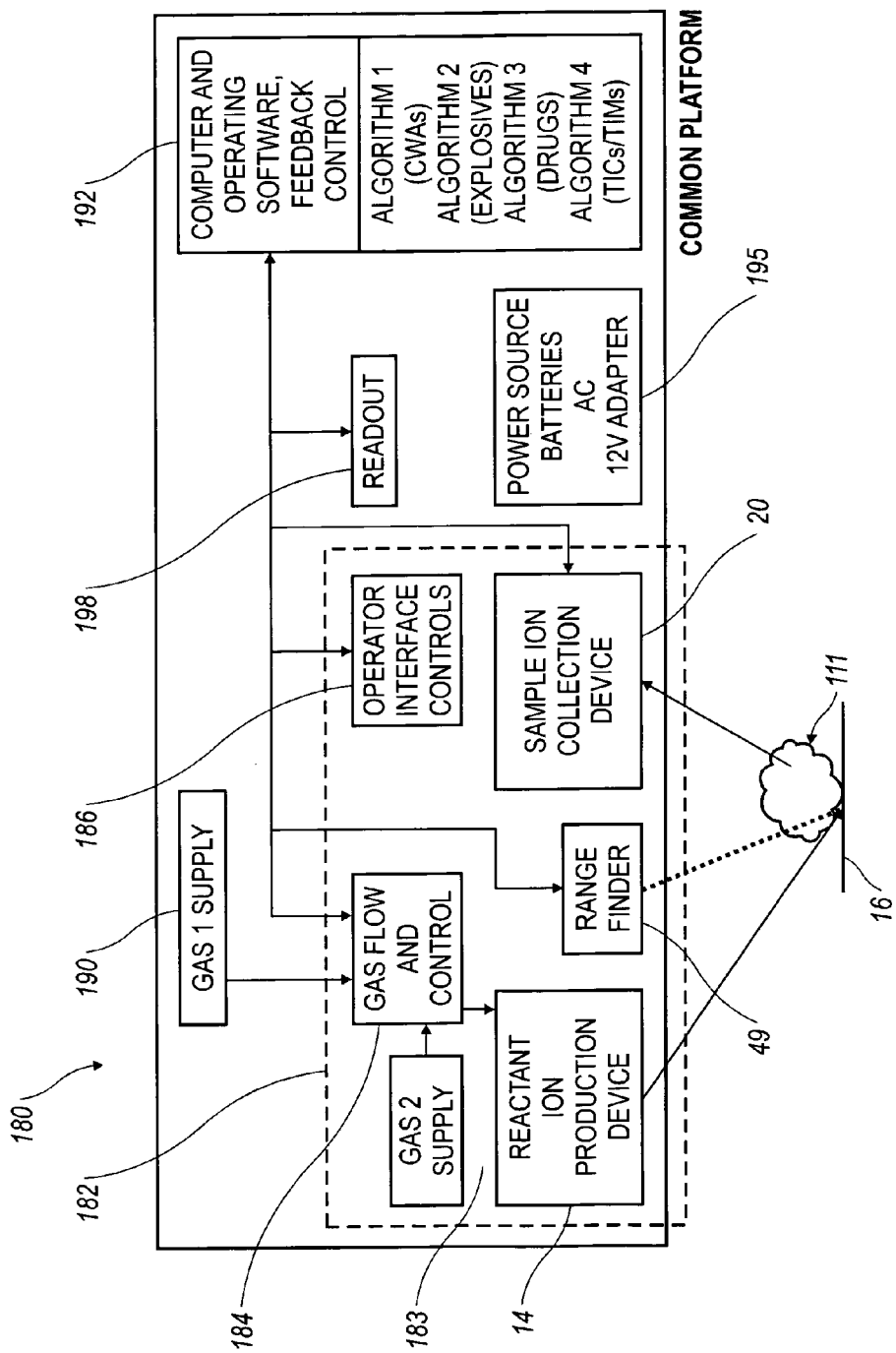
FIG. 11 is a generally schematic diagram of the arrangement of components in an operating system for a detector according to the teachings of this invention.

The components making up the system of this invention may be and preferably are assembled in a manner that facilitates different modes of use. FIG. 11 is a schematic diagram of one embodiment of this invention in which all of the system components are assembled as a fully portable, hand-held detector 180 that contains its own helium supply. A subassembly 183 that includes those components within the dashed line 182 defines a common platform that can be used for each of the different configurations of the system. This common platform includes air and helium valving and gas flow control means 184, reactant ion production means 14, sample ion collection, detection and identification means 20, and an operator interface and control unit 186.

An on-board helium supply 190, conveniently in the form of a disposable cartridge containing pressurized gas, provides an adequate supply for a limited number of analyses and thus is suitable for use by first responders, law enforcement and military personnel. A computer 192 together with its operating software controls the functioning of the system including helium and air flows and the operating parameters of the reactant ion source 14 that in turn depend upon whether the system is being operated in a continuous or in a cyclic mode. The computer also uses information from rangefinder 49 (standoff distance from the ion source outlet to the surface that is being investigated) and sensor information to control reactant ion production and surface sample ion collection to maximize both. The software carried in computer 192 employs a number of different algorithms to distinguish between and to identify ions and charged molecular fragments that result from the impingement of reactant ions, in ion stream 101, upon a surface 16 that has deposited thereon chemical compounds or other agents of interest or concern.

In a preferred embodiment, a number of different algorithms are carried in the computer, a different algorithm for each of different classes of materials. In this case, algorithm 1 is specific to chemical warfare agents, algorithm 2 is specific for explosives, algorithm 3 is specific for drugs of both the prescription and illegal varieties, and algorithm 4 is specific for toxic industrial chemicals and other toxic industrial materials. The system also requires a power source 195 that may include both batteries and a transformer-inverter for AC use. Readout means 198 is arranged to report the results of an analysis, and may be adapted to provide data either in visual form or as a printout. All of the system components reside within a case 199, which can be easily carried and maneuvered during use.

The system of FIG. 11 may also be configured in another mode in which the helium supply tank is separated from the other system components with the helium being supplied from a larger tank carried separately by the system operator. For example, a tank as small as 21 inches in height and 3.5 inches in diameter and weighing on the order of ten pounds, can contain as much as 550 liters of helium. That would allow up to about 30 hours of continuous operation at a use rate of 300 ml/min.

A limited portable configuration may also be employed. In this mode of operation the common platform, as defined in FIG. 11, is assembled within a separate case that is tethered to a stationary base by means of a flexible cable for passing electrical signals and a flexible hose for supplying helium. This configuration provides mobile detection and surface interrogation capability within a fixed radius of a stationary point and avoids any weight or size limitations on the choice of a computer, its operation/detection software, power source and display/printer/data storage devices. It can also better accommodate the largest and most robust libraries of algorithms for distinguishing explosives, drugs, chemical warfare agents, and toxic industrial chemicals from interferents and innocuous substances. This configuration is especially advantageous for use at security and transportation checkpoints to monitor people, baggage, cargo, and material surfaces, as well as for the examination of baggage or incoming deliveries on conveyor belts, and for military, law enforcement, prison and industrial monitoring. The common platform, in whole or in part, and in conjunction with other parts of this configuration, can be used to examine items passing before it, whether such item be baggage or industrially produced items such as pharmaceuticals in order to determine the presence or absence of certain target chemicals in each different use.

Finally, the system can be deployed as a non-portable, bench top detector mode. This arrangement is particularly useful in those applications requiring high volume examination or scanning of field-collected samples, or in those instances in which a detailed scanning and examination of suspect objects is needed Other variations and modifications that are not specifically set out in the description herein will be apparent to those skilled in the art and the described invention is to be limited only by the scope of the following claims.

The invention claimed is:

1. A method for the non-contact detection and analysis of an analyte material comprising:
   passing a first gas through an electrical discharge to produce a stream of charged and energetic species;
   mixing said first gas, now containing charged and energetic gas species, with a second gas, said second gas having at least one component with an ionization potential less than that of said charged and energetic gas species to thereby produce reactant ions of said second gas in a mixed gas stream;
   directing ions contained in the mixed gas stream to form a beam within said gas stream to form a directed gas stream and directing said directed gas stream and ion beam onto an analyte material, at least some of said analyte material having an ionization potential less than those of said reactant ions, to thereby analyze analyte molecules and to form analyte ions; and
   collecting at least a portion of the gas containing analyte ions, and passing the collected portion into a sensor to thereby detect and identify the analyte material;
   wherein said method is performed via a device that comprises a self-contained gas supply and that is portable and hand-held during operation.

2. The method of claim 1 wherein the analyte material is located in an unconfined space.

3. The method of claim 1 wherein the analyte ions are formed by transferring energy from reactant ions in the ion beam to analyte molecules.

4. The method of claim 1 wherein said charged species produced by the electrical discharge are removed from the first gas prior to its mixing with the second gas.

5. The method of claim 1 wherein the analyte material comprises chemical compounds residing substantially on a surface that is located in an unconfined space.

6. The method of claim 1 wherein the first gas is selected from the group consisting of: helium, argon, and mixtures thereof, and wherein the second gas is selected from the group consisting of air, oxygen, nitrogen, and mixtures thereof.

7. The method of claim 1 wherein a dopant compound is mixed with the first gas, before said first gas passes through the electrical discharge.

8. The method of claim 1 wherein a dopant compound is mixed with the second gas.

9. The method of claim 1 wherein said directed gas stream is substantially surrounded by a protective gas sheath.

10. The method of claim 1 wherein the sensor is an ion mobility spectrometer.

11. The method of claim 1 wherein the sensor is a differential mobility spectrometer.

12. The method of claim 1 wherein reactant ions contained in the mixed gas stream are substantially stripped from that stream and are transferred into a stream of a third gas; wherein the ions transferred to said third gas are focused to form a beam within said third gas stream; and wherein said third gas stream and focused ion beam are directed to contact analyte materials.

13. The method of claim 1 wherein the reactant ions in said directed gas stream are caused to be first positive and then negative in a pulsed, cyclic mode.

14. The method of claim 11 wherein said analyte ions are collected in synchronized and pulsed, cyclic mode.

15. The method of claim 12 wherein said sensor is operated in a cyclic mode in synchronization with the collection of said analyte ions.

16. The method of claim 1 wherein reactant ions in said directed gas stream are caused to be first positive and then negative in a pulsed, cyclic mode; wherein for each portion of a cycle during which positive reactant ions are produced, positive analyte ions are collected and passed into the sensor; and wherein for each portion of a cycle during which negative reactant ions are produced, negative analyte ions are collected and directed to the sensor.

17. The method of claim 1 wherein the sensor substantially simultaneously detects positive and negative ions.

18. The method of claim 1 wherein analyte ions are attracted and collected through use of an electric field of opposite charge to that of the analyte ions, and wherein the collected ions are focused and directed to the sensor.

19. The method of claim 1 wherein said sensor includes an ion collection means having an entry port; wherein gas containing analyte ions are drawn into the entry port of said ion collection means by application of a negative pressure to the entry port; and wherein the collected ions are focused and directed to said sensor.

20. The method of claim 1 wherein ions collected and contained in the gas stream passing to said sensor are first stripped from that stream and are transferred into a stream of a different gas, and wherein said different gas is then directed into the sensor.

21. The method of claim 1 wherein a dopant compound in an ionized state is introduced into the collected gas portion entering the sensor.

22. The method of claim 1 wherein the analyte materials reside substantially on a surface and wherein a process, selected from the group consisting of focusing said ion beam and accelerating said ion beam is changed as the distance of travel to said surface varies to thereby maintain the area of the surface impacted by the ion beam substantially constant.

23. The method of claim 1 wherein the location of an analyte ion collection means leading to an entry port of said sensor is varied in response to feedback information from the sensor and from distance of travel information from a rangefinder to thereby maximize the ion content of the sample gas entering the sensor.

24. The method of claim 1 wherein said analyte materials reside substantially on a surface and wherein substantially real-time control and optimization of analyte ion production and collection is obtained by using first information from a rangefinder to substantially continuously determine the distance of travel of said ion beam in said unconfined space and by using second information from said sensor as to the concentration of ions entering said sensor to vary gas flow and to effect at least one ion process control, said ion process control selected from the group consisting of: focusing ions, accelerating ions, repelling ions, attracting ions, and combinations thereof.

25. The method of claim 1 wherein the sensor is a differential mobility spectrometer; wherein the reactant ions in said mixed gas are concentrated into a third gas which then replaces said mixed gas stream.

26. The method of claim 1 wherein the sensor is a differential mobility spectrometer; wherein said focused ion beam is caused to be positive and then negative in a pulsed cyclic mode; and wherein positive and then negative analyte ions are sequentially collected in substantial synchronization with the polarity changes of the focused ion beam.

27. The method of claim 1 further comprising the step of: compressing an analyte ion stream before directing the analyte ions to the sensor.

28. A method for the non-contact detection and analysis of an analyte material located substantially on a surface comprising:
   passing a first gas that is selected from the group consisting of helium, argon and mixtures thereof through an electrical discharge to produce charged and energetic molecular gas species;
   mixing said first gas with a second gas, said second gas being reactive with the charged and/or energetic gas species of said first gas to produce reactant ions of the second gas;
   focusing the reactant ions contained in the mixed gas stream to form a beam;
   directing the beam and the mixed gas stream onto said surface to react with analyte molecules; and
   collecting at least a portion of the mixed gas stream from an area proximate to the surface, said collected portion containing analyte ions, and passing the collected portion into a differential mobility spectrometer to identify and quantify the analyte molecules;
   wherein said method is performed via a device that comprises a self-contained gas supply and that is portable and hand-held during operation.

29. The method of claim 28 wherein the analyte material is substantially located on a surface in an unconfined space.

30. The method of claim 28 wherein said directed gas stream is substantially surrounded by a protective gas sheath.

31. The method of claim 28 wherein a dopant compound is mixed with the first gas before passing it through the electrical discharge.

32. The method of claim 28 wherein a dopant compound is mixed with the second gas.

33. The method of claim 28 wherein ions contained in the mixed gas stream are substantially stripped from that stream and are transferred into a stream of a third gas, wherein the ions transferred to said third gas are focused to form a beam within said third gas stream, and wherein said third gas stream and focused ion beam are directed to contact said surface.

34. The method of claim 28 wherein the ions in said directed gas stream are caused to be first positive and then negative in a pulsed, cyclic mode and wherein said differential mobility spectrometer is operated in a complementary similar and synchronized, pulsed, cyclic mode.

35. The method of claim 28 wherein reactant ions in said directed gas stream are caused to be first positive and then negative in a pulsed, cyclic mode, wherein the differential mobility spectrometer includes ion collection means, and wherein the ion collection means is operated in a complementary similar and pulsed cyclic mode in synchronization with the cycle of said directed gas stream.

36. The method of claim 28 wherein reactant ions in said directed gas stream are caused to be first positive and then negative in a pulsed, cyclic mode, wherein for each portion of a cycle during which positive reactant ions are produced, positive analyte ions are collected and passed into the spectrometer, and wherein for each portion of a cycle during which negative reactant ions are produced, negative analyte ions are collected and passed into the spectrometer.

37. The method of claim 28 wherein said differential mobility spectrometer is operated in a mode wherein said spectrometer substantially simultaneously detects positive and negative ions.

38. The method of claim 28 wherein analyte ions are attracted and collected through the use of an electric field of opposite charge to that of the analyte ions, and wherein the collected ions are focused and directed to the spectrometer.

39. The method of claim 28 wherein said differential mobility spectrometer further comprises an ion collection means having an entry port, wherein gas containing analyte ions are drawn into the entry port of said ion collection means by application of a negative pressure to the entry port, and wherein the collected ions are focused and directed to said spectrometer.

40. The method of claim 28 wherein ions contained in the gas stream passing to said differential mobility spectrometer are first substantially stripped from said gas stream and are transferred into a stream of a different gas, and wherein said different gas stream is then directed into said spectrometer.

41. The method of claim 28 wherein a dopant compound in an ionized state is introduced into the collected gas stream that is directed to said differential mobility spectrometer.

42. The method of claim 28 wherein the focus of said ion beam is changed as the distance of travel to said surface varies to thereby maintain the area of the surface impacted by the ion beam substantially constant.

43. The method of claim 28 wherein the location of an analyte ion collections means leading to entry port of said spectrometer is varied in response to feedback information from said spectrometer and distance information from a rangefinder to thereby maximize the analyte ion content of the sample gas entering the spectrometer.

44. The method of claim 28 wherein said analyte material resides substantially on a surface, and wherein real-time control and optimization of analyte ion production and collection is obtained by using first information from a rangefinder to substantially continuously determine the distance of ion beam travel through the unconfined space and by using second information from the differential mobility spectrometer as to the concentration of ions entering said spectrometer to vary gas flow and to effect at least one ion process control, said ion process control selected from the group consisting of: focusing ions, accelerating ions, repelling ions, attracting ions, and combinations thereof.

45. The method of claim 28 wherein an analyte ion stream is compressed and directed to the differential mobility spectrometer.

46. An ion production device comprising:
an elongated containment means having an inlet for the introduction of a first gas at an upstream end thereof, and exit for an ion and gas stream at a downstream end thereof, and an inlet for the introduction of a second gas located intermediate the upstream and downstream ends;
electrical discharge means positioned at the upstream end, said discharge means and first gas inlet means arranged to cause flow of the first gas through said discharge;
a mixing and reaction space downstream of said second gas entry, said space arranged to allow mixing of said first and second gas streams and to allow reaction of charged and/or energetic species remaining in said first gas with said second gas to produce reactant ions;
means to urge the reactant ions into a substantially conical ion beam such that ion beam together with said mixed gases issue from the containment means through said exit as a substantially conical beam;
wherein the device further comprises a self-contained gas supply and is portable and hand-held during operation.

47. The device of claim 46, further comprising a means adjacent said exit for providing a substantially conical sheath of protective gas to surround said ion beam, said means including a substantially conically tapered wall terminating at its downstream end to form a ring orifice substantially circling said exit and means to introduce a protective gas into a manifold space formed between the outer side of said tapered and the interior of said containment means.

48. The device of claim 46 wherein said containment means are substantially cylindrical, said device including a plurality of focusing and accelerating electrodes downstream of said mixing and reaction space, each said electrode providing an electric field circling the interior of said containment means at the site of the electrode.

49. The device of claim 48 wherein said containment means are substantially cylindrical and wherein a central portion of said containment means is formed as a venturi with an entry for gas at the venturi throat.

50. The device of claim 46 wherein said containment means are substantially cylindrical, said device including an ion concentration and gas exchange means located downstream of said mixing and reactant space.

51. The device of claim 50 wherein said ion concentration and gas exchange means includes a cylindrical outer wall, a central, axially aligned electrode carrier and a cylindrical partition member therebetween, said partition member forming a first annular space that is open at its upstream end to accept gas from said mixing and reactant space, a second annular space closed at its upstream end and provided with a source of exchange gas, said cylindrical partition having at least one port arranged to allow ion and gas flow between the first and the second annular space and electrode means arranged to urge ions through the port and into the exchange gas stream.

52. The device of claim 51, further comprising at least two ports in said cylindrical partition for ion and gas flow; first electrodes located in said first annular space opposite each port, said first electrodes having the same polarity as the ions being separated from the incoming gas stream; and second electrodes located in said second annular space on said central axially aligned electrode carrier opposite each port, said second electrodes having an opposite polarity to that of the ions being separated from the incoming gas stream.

53. The device of claim 51, further comprising pressure adjusting means to cause a slow bleed of gas from said second annular space, through said ports, and into said annular first space.

54. The device of claim 46, further comprising a means to cause the reactant ions in said directed gas stream to be first positive and then negative in a pulsed, cyclic mode.

55. The device of claim 46, further comprising a means to continuously measure the distance from said containment means exit to the site of a sample material.

56. The device of claim 46, further comprising a means to introduce a dopant into said first gas upstream of said electrical discharge means.

57. The device of claim 46, further comprising a means to introduce a dopant into said second gas prior to mixing with said first gas.

58. The device of claim 46 wherein the device further comprises a self-contained helium supply.

59. A method for producing ions of an analyte material, comprising:
passing a first gas stream through an electrical discharge to produce ions and energetic species of said gas;
mixing the first gas stream with a second gas that has an ionization potential less than the ionization potential of said energetic species thereby producing reactant ions of said second gas; said reactant ions having ionization potentials greater than the ionization potentials of said analyte;
focusing said reactant ions to form a reactant ion beam within a flowing gas stream;
directing said gas stream and ion beam into contact with said analyte material; and
forming analyte ions by transferring energy from reactant ions in said ion beam to the analyte material;
wherein said method is performed via a device that comprises a self-contained gas supply and that is portable and hand-held during operation.

60. The method of claim 59 wherein said first gas is selected from the group consisting of helium, argon, and mixtures thereof; and said second gas is selected from the group consisting of air, oxygen, nitrogen, and mixtures thereof.

61. The method of claim 59 wherein ions contained in the mixed gas stream are substantially stripped from the mixed gas stream and are transferred into a stream of a third gas and are focused to form a beam within said third gas stream, said third gas stream and focused ion beam thereafter being directed into contact with said analyte material.

62. The method of claim 59 wherein said analyte material substantially resides on a surface and wherein the distance of travel of the ion beam is substantially continuously determined and is used to provide substantially real-time control and optimization of said reactant ion production.

63. The method of claim 59 wherein said analyte material is located substantially on a surface and wherein said gas stream and ion beam is substantially surrounded by a protective gas sheath.

64. The method of claim 59 wherein a dopant compound is mixed with the first gas before passing it through the electrical charge.

65. The method of claim 64 wherein a dopant compound is mixed with the second gas.

66. The method of claim 59 wherein said reactant ion beam is caused to be positive and then negative in a pulsed, cyclic mode.

67. The method of claim 59 wherein said analyte material is located substantially on a surface in an unconfined space.

68. The method of claim 59, further comprising the steps of: compressing an analyte ion stream and transmitting the analyte ions to a sensor.

69. A device for the non-contact detection and analysis of an analyte material, comprising:
an ion source including a containment means having an upstream end and a downstream end;
an inlet for a first gas disposed at the upstream end of the containment means;
an exit port at the downstream end, and an inlet for a second gas disposed intermediate the containment means ends;
electrical discharge means positioned at the upstream end, said discharge means and first gas inlet arranged to cause flow of the first gas through said discharge;
a mixing and reaction space downstream of the second gas inlet, said space arranged to allow mixing of said first gas and said second gas and to allow reaction of charged and/or energetic species, resulting from passage of said first gas through the electrical discharge, with said second gas to produce reactant ions;
focusing means disposed downstream of said mixing and reaction space, said means arranged to urge the reactant ions into a coherent beam;
means at said exit port to direct said ion beam into contact with analyte materials in said unconfined space to thereby form sample analyte ions by transferring energy from reactant ions in said ion beam to the analyte material; and
an ion collection means and a sensor operably connected to said ion source, said ion collection means having inlet port means arranged relative to said exit port of said ion source to collect at least a portion of the sample analyte ions and said sensor including means to identify and quantify the analyte material;
wherein the device further comprises a self-contained gas supply and is portable and hand-held during operation.

70. The device of claim 69 wherein the analyte material is located in a substantially unconfined space.

71. The device of claim 69 wherein said containment means is formed as an elongated cylinder and includes at least two filtering electrodes of differing polarity placed between the electrical discharge means and the mixing and reaction space, said filtering electrodes being arranged to remove either positive ions, negative ions, or both, from the first gas prior to its mixing with the second gas.

72. The device of claim 69 wherein said containment means is formed as an elongated cylinder and wherein the focusing means comprises at least one electrode, each said electrode providing an electric field substantially circling the interior of said containment means proximate to the electrode.

73. The device of claim 69, further comprising said containment means is formed as a cylinder, said containment means including a substantially conically tapered partition disposed within said cylinder at the downstream end thereof, the apex end of said partition being open and forming a ring orifice in association with said exit port, the partition further defining a manifold formed between the exterior partition wall and the interior wall of said cylinder, and an inlet port arranged to allow communication between the manifold and an external source of a sheath gas, said sheath gas exiting the manifold through the ring orifice to form a gas shield between the atmosphere and the ion beam.

74. The device of claim 69, further comprising ion concentration and gas exchange means positioned downstream from said mixing and reaction space, said ions concentration and gas exchange means comprising a substantially cylindrical outer wall, a substantially central axially aligned electrode carrier and a cylindrical partition member therebetween, said partition member forming a first annular space that is open at its upstream end to accept gas from said mixing and reactant space, a second annular space closed at its upstream end and provided with a source of exchange gas, said cylindrical partition having at least one port arranged to allow ion and gas flow between the first and the second annular space and electrode means arranged to urge ions through the port and into the exchange gas stream.

75. The device of claim 74, further comprising at least two ports in said substantially cylindrical partition for ion and gas flow, first electrodes located in said first annular space opposite each port, said first electrodes having the same polarity as the ions in the incoming gas stream; second electrodes located in said second annular space on said central axially aligned electrode carrier opposite each port, said second electrodes having an opposite polarity to that of the ions in the incoming gas stream, and pressure adjusting means to cause a slow bleed of gas from said second annular space, through said ports, and into said first annular space.

76. The device of claim 69 wherein said analyte material resides substantially on a surface and wherein the device includes a rangefinder means and a processing unit, said rangefinder adapted to determine the distance between the exit port and said surface and to transmit that information to a processing unit, said processing unit adjusting the acceleration and focusing functions of said focusing and accelerating electrode means in response to rangefinder data to maintain the area of the surface impacted by the ion beam substantially constant as the distance between the exit port and the surface is varied.

77. The device of claim 69 wherein the sensor is a differential mobility spectrometer having a port for the entry of gas samples.

78. The device of claim 69 wherein the sensor is an ion mobility sensor.

79. The device of claim 69 wherein said analyte material resides substantially on a surface and wherein said ion collection means is arranged relative to the exit port of said ion source to maximize the concentration of ions in a gas sample drawn into the sensor.

80. The device of claim 69, further comprising means to maximize concentration of ions comprising servo means adapted to change the attitude and/or location of said ion collection means relative to the ion source exit port in response to feedback information from said sensor.

81. The device of claim 69, further comprising a means to maximize concentration of reactant ions comprising a rangefinder means and a processing unit, said rangefinder adapted to determine the distance between the exit port of said ion source and said surface that carries analyte materials, said processing unit adjusting the acceleration and focusing functions of said focusing and accelerating electrode means in response to rangefinder data to maintain the area of the surface impacted by the ion beam substantially constant as the distance between the exit port and surface is varied.

82. The device of claim 69, further comprising a means for real-time control and optimization of analyte ion production and collection using first information from a rangefinder to continuously determine the distance of travel of said ion beam, and second information from said sensor as to the concentration of ions entering said sensor to thereby vary gas flow and to effect at least one ion process control, said ion process control selected from the group consisting of focusing ions, accelerating ions, repelling ions, attracting ions, and combinations thereof.

83. The device of claim 82 wherein the sensor is a differential mobility spectrometer.

84. The device of claim 69, further comprising a means to draw a gas stream containing analyte ions into an entry port of said ion collection means by applying a negative pressure to the entry port of said collection means.

85. The device of claim 84, further comprising a means to introduce a dopant compound in an ionized state into said gas stream.

86. The device of claim 84 wherein the sensor is a differential mobility spectrometer.

87. The device of claim 69 wherein said port for entry of gas samples includes means to attract and collect sample ions by application of an electric field of opposite charge to that of the sample ions.

88. The device of claim 69 wherein said ion source and said ion collection means are operated in a cyclic mode, said ion source arranged to sequentially produce reactant ions of a first polarity and of an opposite polarity, and said spectrometer synchronously arranged to attract and collect sample ions of said first polarity and then of said opposite polarity.

89. The device of claim 69 wherein said sensor is arranged to operate in a mode to substantially simultaneously detect positive and negative ions.

90. The device of claim 69 wherein said sensor is a differential mobility spectrometer; wherein said ion beam is caused to be positive and then negative in a pulsed cyclic mode; and wherein, for each portion of a cycle in which the ion beam is either positive or negative, the ion collection means are operated in a synchronized manner to sequentially collect positive and then negative analyte ions.

91. The device of claim 69 in which said containment means are generally cylindrical and wherein a central portion of the containment means is formed as a venturi with an entry for gas at the venturi throat.

92. The device of claim 69 wherein said sensor is a differential mobility spectrometer having a port for the entry of gas samples, wherein analyte ions are attracted to and collected by said ion collection means through use of an electric field of opposite charge to that of the sample ions, and wherein said collected analyte ions are focused and moved to the entry port of said spectrometer.

93. The device of claim 69 wherein said sensor is a differential mobility spectrometer having a port for the entry of gas samples; wherein analyte ions are drawn to said ion collection means by way of a negative pressure; an wherein said collected analyte ions are focused and moved to the entry port of said spectrometer.

94. The device of claim 69, further comprising a means to remove analyte ions from a gas stream entering said ion collection means and to transfer said removed analyte ions into a stream of a different gas, and means to direct that different gas into said sensor.

95. The device of claim 69, further comprising a means to introduce a dopant compound in an ionized state into said collected analyte ions.

96. The device of claim 69, further comprising a means to change the focus of said ion beam as the distance between said ion source exit port and said analyte materials varies to thereby maintain the area of the surface impacted by said ion beam substantially constant.

97. The device of claim 69 wherein said sensor is a differential mobility spectrometer and wherein the location of said ion collection inlet port is varied in response to feedback information from said spectrometer and from distance of ion beam travel from a rangefinder to thereby maximize the reactant or analyte ion content of the sample gas entering the spectrometer.

98. The device of claim 69, further comprising a means for introducing a dopant into said mixing and reaction space.

99. The device of claim 69 wherein the gas supply is helium.

100. The device of claim 69 wherein an analyte ion stream is compressed and directed to the sensor.

101. An ion production device comprising:
an elongated containment means having an inlet for the introduction of a first gas at an upstream end thereof, and exit for an ion and gas stream at a downstream end thereof, and an inlet for the introduction of a second gas located intermediate the upstream and downstream ends;
electrical discharge means positioned at the upstream end, said discharge means and first gas inlet means arranged to cause flow of the first gas through said discharge;
a mixing and reaction space downstream of said second gas entry, said space arranged to allow mixing of said first and second gas streams and to allow reaction of charged and/or energetic species remaining in said first gas with said second gas to produce reactant ions;
means to urge the reactant ions into a substantially conical ion beam such that ion beam together with said mixed gases issue from the containment means through said exit as a substantially conical beam;
wherein the device further comprises a self-contained gas supply.

102. The device according to claim 101, wherein the device is portable.

103. The device according to claim 101, wherein the device is hand-held during operation.

104. A hand-held ion production device comprising:
an elongated containment means having an inlet for the introduction of a first gas at an upstream end thereof, and exit for an ion and gas stream at a downstream end thereof, and an inlet for the introduction of a second gas located intermediate the upstream and downstream ends;
electrical discharge means positioned at the upstream end, said discharge means and first gas inlet means arranged to cause flow of the first gas through said discharge;

a mixing and reaction space downstream of said second gas entry, said space arranged to allow mixing of said first and second gas streams and to allow reaction of charged and/or energetic species remaining in said first gas with said second gas to produce reactant ions;

means to urge the reactant ions into a substantially conical ion beam such that ion beam together with said mixed gases issue from the containment means through said exit as a substantially conical beam;

wherein the device is hand-held during operation.

105. A method for the non-contact detection and analysis of an analyte material comprising:

directing a hand-held device to perform the following operations:

passing a first gas through an electrical discharge to produce a stream of charged and energetic species;

mixing said first gas, now containing charged and energetic gas species, with a second gas, said second gas having at least one component with an ionization potential less than that of said charged and energetic gas species to thereby produce reactant ions of said second gas in a mixed gas stream;

directing ions contained in the mixed gas stream to form a beam within said gas stream to form a directed gas stream and directing said directed gas stream and ion beam onto an analyte material, at least some of said analyte material having an ionization potential less than those of said reactant ions, to thereby analyze analyte molecules and to form analyte ions; and collecting at least a portion of the gas containing analyte ions, and passing the collected portion into a sensor to thereby detect and identify the analyte material.

106. A method for the non-contact detection and analysis of an analyte material located substantially on a surface comprising:

directing a hand-held device to perform the following operations:

passing a first gas that is selected from the group consisting of helium, argon and mixtures thereof through an electrical discharge to produce charged and energetic molecular gas species;

mixing said first gas with a second gas, said second gas being reactive with the charged and/or energetic gas species of said first gas to produce reactant ions of the second gas;

focusing the reactant ions contained in the mixed gas stream to form a beam;

directing the beam and the mixed gas stream onto said surface to react with analyte molecules; and collecting at least a portion of the mixed gas stream from an area proximate to the surface, said collected portion containing analyte ions, and passing the collected portion into a differential mobility spectrometer to identify and quantify the analyte molecules.

107. A method for producing ions of an analyte material, comprising:

directing a hand-held device to perform the following operations:

passing a first gas stream through an electrical discharge to produce ions and energetic species of said gas;

mixing the first gas stream with a second gas that has an ionization potential less than the ionization potential of said energetic species thereby producing reactant ions of said second gas; said reactant ions having ionization potentials greater than the ionization potentials of said analyte;

focusing said reactant ions to form a reactant ion beam within a flowing gas stream;

directing said gas stream and ion beam into contact with said analyte material; and forming analyte ions by transferring energy from reactant ions in said ion beam to the analyte material.

108. A device for the non-contact detection and analysis of an analyte material, comprising:

an ion source including a containment means having an upstream end and a downstream end;

an inlet for a first gas disposed at the upstream end of the containment means;

an exit port at the downstream end, and an inlet for a second gas disposed intermediate the containment means ends;

electrical discharge means positioned at the upstream end, said discharge means and first gas inlet arranged to cause flow of the first gas through said discharge;

a mixing and reaction space downstream of the second gas inlet, said space arranged to allow mixing of said first gas and said second gas and to allow reaction of charged and/or energetic species, resulting from passage of said first gas through the electrical discharge, with said second gas to produce reactant ions;

focusing means disposed downstream of said mixing and reaction space, said means arranged to urge the reactant ions into a coherent beam;

means at said exit port to direct said ion beam into contact with analyte materials in said unconfined space to thereby form sample analyte ions by transferring energy from reactant ions in said ion beam to the analyte material; and an ion collection means and a sensor operably connected to said ion source, said ion collection means having inlet port means arranged relative to said exit port of said ion source to collect at least a portion of the sample analyte ions and said sensor including means to identify and quantify the analyte material;

wherein the device further comprises a self-contained gas supply.

109. The device according to claim 108, wherein the device is portable.

110. The device according to claim 108, wherein the device is hand-held during operation.

111. A hand-held device for the non-contact detection and analysis of an analyte material, comprising:

an ion source including a containment means having an upstream end and a downstream end;

an inlet for a first gas disposed at the upstream end of the containment means;

an exit port at the downstream end, and an inlet for a second gas disposed intermediate the containment means ends;

electrical discharge means positioned at the upstream end, said discharge means and first gas inlet arranged to cause flow of the first gas through said discharge;

a mixing and reaction space downstream of the second gas inlet, said space arranged to allow mixing of said first gas and said second gas and to allow reaction of charged and/or energetic species, resulting from passage of said first gas through the electrical discharge, with said second gas to produce reactant ions;

focusing means disposed downstream of said mixing and reaction space, said means arranged to urge the reactant ions into a coherent beam;

means at said exit port to direct said ion beam into contact with analyte materials in said unconfined space to thereby form sample analyte ions by transferring energy from reactant ions in said ion beam to the analyte material; and an ion collection means and a sensor operably connected to said ion source, said ion collection means having inlet port means arranged relative to said exit port of said ion source to collect at least a portion of the sample analyte ions and said sensor including means to identify and quantify the analyte material;

wherein the device is hand-held during operation.

* * * * *